United States Patent [19]

Woods, Jr. et al.

[11] Patent Number: 5,501,859

[45] Date of Patent: Mar. 26, 1996

[54] ABSORBABLE MAGNESIUM COMPOSITION AND METHOD OF USING SAME

[75] Inventors: Walter T. Woods, Jr., R.R. 1, Box 13, Chatham, Ill. 62629; Charles S. Lichtman, Birmingham, Ala.

[73] Assignee: Walter T. Woods, Jr., Springfield, Ill.

[21] Appl. No.: 215,910

[22] Filed: Mar. 22, 1994

[51] Int. Cl.$^6$ .................................................. A61K 9/127
[52] U.S. Cl. .......................... 424/450; 424/681; 424/682; 424/697
[58] Field of Search .................................. 424/450, 681, 424/682, 697

[56] References Cited

U.S. PATENT DOCUMENTS

| | | | |
|---|---|---|---|
| 3,882,232 | 5/1975 | Pendergrast | 424/158 |
| 4,235,871 | 11/1980 | Papahadjopoulos | 424/450 |
| 4,522,803 | 6/1985 | Lenk | 424/1.1 |
| 4,762,720 | 8/1988 | Jizomoto | 424/450 |
| 5,035,898 | 7/1991 | Chang | 424/474 |
| 5,227,170 | 7/1993 | Sullivan | 424/450 |

*Primary Examiner*—Gollamudi S. Kishore
*Attorney, Agent, or Firm*—Hill, Steadman & Simpson

[57] ABSTRACT

An absorbable magnesium composition is provided. The absorbable magnesium composition includes a magnesium salt in a liposomal material encapsulating the magnesium salt. A method of using as well as a method of preparing the magnesium composition of the present invention is also provided.

15 Claims, No Drawings

ABSORBABLE MAGNESIUM COMPOSITION AND METHOD OF USING SAME

BACKGROUND OF THE INVENTION

The present invention relates generally to the treatment of diseases and dysfunctions. More particularly, the present invention relates to the treatment of magnesium deficiencies.

Magnesium is the fourth most plentiful cation in the body (total body content about 2,000 mEq in a 70-kg man), but only 1% exists in the ECF. While 50% of the total body magnesium is found in bone and is not readily exchangeable with magnesium in ECF; the remainder is intracellular. Normal serum values range from 1.6 and 2.1 mEq/L(1.9 and 2.5 mg/dl). *Merck Manual*, 16th Ed., p. 1016 (1992).

A wide variety of enzymes including phosphatases (e.g., ATP and alkaline phosphatase) are magnesium activated or dependent (magnesium is required by all enzymatic processes involving ATP). Magnesium is required for thiamine pyrophosphate cofactor activity and appears to stabilize macromolecular structure (e.g., DNA and RNA). Magnesium is also related to calcium and potassium metabolism in an intimate but poorly understood fashion.

Due to the important role magnesium plays in a mammal's body, magnesium deficiency may result in physiologic dysfunctions. A low blood concentration of magnesium is known as hypomagnesemia. Hypomagnesemia is generally defined as a serum magnesium concentration less than 1.6 mEq/L (less than 1.9 mg/dL). Hypomagnesemia is often present when magnesium depletion is severe. *Merck Manual*, p. 1017.

Magnesium depletion usually results from inadequate intake plus impairment of renal or gut absorption. Clinically significant magnesium deficiency most commonly is associated with: (1) malabsorption syndromes from all causes; (2) protein-calorie malnutrition; (3) parathyroid disease; (4) chronic alcoholism; and (5) chronic diarrhea. Id.

The most common treatment for magnesium deficiency is the administration of magnesium salts. However, existing magnesium preparations are poorly absorbed from the digestive system into the blood, accounting for the well known laxative effect of magnesium. Taken orally, magnesium salts remain unabsorbed in the intestine where they cause water to accumulate, leading to diarrhea. As a result, the magnesium salts must be administered directly into the blood by an intravenous route. While this intravenous route may provide an effective means to administer magnesium salts into the blood, naturally, it is an inconvenient and burdensome method.

Even if magnesium concentrations are "normal", certain disease states can benefit from elevated blood levels of magnesium. Such disease states include cardiovascular disease.

Therefore, a need exists for an improved composition and methods for elevating blood levels in a patient.

SUMMARY OF THE INVENTION

The present invention provides improved methods and compositions for providing magnesium to a patient. More particularly, the present invention provides an absorbable magnesium composition that can be effectively administered orally to patients in order to raise the blood level of magnesium in such patients.

The absorbable magnesium composition of the present invention includes a magnesium salt in a liposomal material surrounding the magnesium salt. In an embodiment, the magnesium salt may be either magnesium sulfate or magnesium chloride.

In an embodiment, the absorbable magnesium composition contains magnesium salt in an amount ranging from about 0.1 to 2.0 moles per liter.

In an embodiment, the liposomal material is a phospholipid.

The present invention also provides a method for raising blood levels of magnesium in a patient. The method includes the step of administering an absorbable magnesium composition having a magnesium salt encased in a liposomal material.

In an embodiment, the absorbable magnesium composition is administered in a dosage ranging from about 1 to 50 milligrams per kilogram body weight.

The present invention also provides a method for making an absorbable magnesium composition. The method includes the steps of providing a magnesium salt and surrounding the magnesium salt with a liposomal material. In an embodiment, the magnesium salt may be either a magnesium sulfate or a magnesium chloride.

An advantage of the present invention is that it provides an absorbable magnesium composition that may be administered orally to a patient. This oral administration provides inherent advantages over the previously used intravenous route.

Another advantage of the present invention is that it provides a magnesium composition having a lipid coating that facilitates absorption through the intestinal wall and transports magnesium into the blood with efficiency exceeding that of existing preparations.

Still further, an advantage of the present invention is that it utilizes a carrier system that has no undesirable side effects.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides an absorbable magnesium composition and methods of using and making same. The absorbable magnesium composition of the present invention includes a magnesium salt and a liposomal material surrounding the magnesium salt. Preferably, the magnesium salt is either magnesium sulfate or magnesium chloride.

As stated above, existing magnesium preparations are poorly absorbed from the digestive system into the blood. The cells that line the digestive tract are the barrier that prevents magnesium from diffusing into the blood. The major structural component of these cells is lipid. The inventor has discovered that particles with high lipid content migrate through these cells with relative ease compared to more polar molecules. Accordingly, by surrounding or coating a magnesium salt with a liposomal material, a readily absorbable composition is provided.

A suitable amount of the magnesium sulfate present in the absorbable magnesium composition depends on maximum stability of magnesium sulfate in water. In an embodiment, the absorbable magnesium composition contains magnesium salt in an amount ranging from about 0.1 to 2.0 moles per liter.

The amount of liposomal material surrounding the magnesium salt depends on the amount of magnesium salt utilized. In an embodiment, the liposomal material is present in an amount ranging from about 1.0 to 50 millimoles per liter (in the form of 1-palmitoyl-2-oleoyl-phosphatidylcholine).

Those skilled in the art will appreciate that a variety of liposomal materials may be used in the present invention. In an embodiment, the liposomal material is phospholipid particles known as liposomes. The magnesium salts of the present invention are encased in the liposomes. The liposomes form a lipid coating that facilitates absorption through the intestinal wall. The lipid coating transports magnesium into the blood with efficiency exceeding that of existing preparations. Notably, the inventor has observed no undesirable side effects from this carrier system.

Liposomes that may be used in the present invention can be prepared using conventional methods. For example, the liposomes that may be used in the present invention may be prepared pursuant to the method set forth in MacDonald et al, *Small-Volume Extrusion Apparatus for Preparation of Large, Unilamellar Vesicles*, 1061 Biochimica et Biophysica Acta, 297, 297–303 (1991). This article is hereby incorporated by reference.

The present invention also provides a method for raising blood levels of magnesium in a patient. The method of the present invention includes the step of enterally administering an absorbable magnesium composition having a magnesium salt encased in a liposomal material.

The appropriate dosage to be administered to a patient depends on the particular patient being treated. Naturally, when the patient is suffering from a severe case of hypomagnesemia, a large amount of magnesium salt may be needed to increase the magnesium within the blood stream.

The present invention may also provide benefits to those with normal magnesium concentrations. In such patients, raising the blood level of magnesium has therapeutic effects. For example, the present invention may provide therapeutic effects in cardiovascular disease situations. In an embodiment, the absorbable magnesium composition is administered to a patient in a dosage ranging from about 1 to 50 milligrams per kilogram body weight. In a preferred embodiment, the absorbable magnesium composition is administered to a patient in a dosage ranging from 1 to 10 milligrams per kilogram body weight.

Unlike prior treatments, the absorbable magnesium composition of the present invention can be administered enterally.

The present invention further provides a method for making an absorbable magnesium composition. This method includes the steps of providing a magnesium salt and surrounding the magnesium salt with a liposomal material. Preferably, the magnesium salt is either a magnesium sulfate or a magnesium chloride.

By way of example, and not limitation, an example detailing the preparation of the composition of the present invention will now be given.

Initially, 100 mg 1-palmitoyl-2-oleoyl-phosphatidylcholine (PC, Sigma) was dissolved in 5 ml chloroform. The resulting composition was dried under a stream of nitrogen and kept under vacuum for at least 1 hour to remove residual solvent. Then, lipid was hydrated at a concentration of 16 mM in buffer. The buffer consisted of 20 MM Tris-HCl, pH 7.5 (Sigma) and 1.0 M $MgCl_2$ (Baker Analyzed). The composition was next freeze-thawed ten times in a solid $CO_2$/ ETOH bath to ensure solute equilibration between trapped and bulk solution. Lastly, the composition was extruded, in batches, through a polycarbonate filter (pore= 100 nm); 19 passes were completed.

By further way of example, and not limitation, experiments demonstrating the present invention will now be given.

EXPERIMENT #1

Baseline serum $Mg^{++}$ concentration was measured in a tail vein blood sample from a 700 g Sprague Dawley male rat (Sigma Diagnostics). Blood was expressed from the tail into heparinized capillary tubes, centrifuged and serum separated.

The rat received 3 ml. of liposomes via intragastric tubes. Five minutes later a 1.0 ml. sample of tail vein blood was expressed into a heparin solution. A 1.0 ml. sample of abdominal interstitial fluid was also collected. Serum $Mg^{++}$ was determined on both samples.

| Experiment #1 | $Mg^{2+}$ millimoles/liter |
| --- | --- |
| Control rat serum | 1.05, 1.06 |
| Post liposomes orally, serum | 11.0, 9.49, 12.68 |
| Post-liposomes orally, abdominal fluid | 12.27, 12.83. 12.84 |

This experiment demonstrates that the treatment of the present invention raised blood magnesium ten fold within 5 minutes.

EXPERIMENT #2

Baseline serum $Mg^{++}$ concentration was measured in a tail vein blood sample from a 700 g Sprague Dawley male rat (Sigma Diagnostics). Blood was expressed from the tail into heparinized capillary tubes, centrifuged and serum separated.

The rat received via intragastric tube 3.0 ml. of a 1:10 dilution (with water) of the stock liposomes. A 1.0 ml. blood sample was collected 1 hour later.

The rat then received via intragastric tube 3 ml. of a 1:2 dilution (with water) of the stock liposomes. A 1.0 ml. blood sample was collected via the tail 30 minutes later.

The rat then received via intragastric tube 1.5 ml. of the stock liposomes. A 1.0 ml. blood sample was collected via the tail 30 minutes later.

| Experiment #2 | $Mg^{2+}$ millimoles/liter |
| --- | --- |
| Control serum | 0.83, 0.83, 0.87 |
| Post-1/10 dilution of liposomes orally | 0.83, 0.84, 0.84 |
| Post-1/1 dilution of liposomes orally | 1.07, 1.08., 1.06 |
| Post-undiluted liposomes orally | 1.46, 1.51., 1.57 |

This experiment shows that increases in serum magnesium concentration correlated with increases in oral doses of liposomes.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A liposomal composition consisting essentially of:
   a therapeutically effective amount of a magnesium salt; and
   liposome forming lipids in an amount sufficient to encapsulate the magnesium salt.

2. The liposomal composition of claim 1 wherein the magnesium salt is present in an amount ranging from about 0.1 to 2.0 moles per liter.

3. The liposomal composition of claim 1 wherein the liposome forming lipids are present in an amount ranging from about 1.0 to 50 millimoles per liter.

4. The liposomal composition of claim 1 wherein the magnesium salt is selected from the group consisting of magnesium sulfate and magnesium chloride.

5. The liposomal composition of claim 1 wherein the liposome forming lipids are phospholipids particles.

6. A method for raising blood levels of magnesium beyond a starting level in a patient in need of same comprising the step of enterally administering to the patient a liposomal composition comprising a therapeutically effective amount of a magnesium salt, and liposome forming lipids in an amount sufficient to encapsulate the magnesium salt.

7. The method of claim 6 wherein the magnesium salt is present in an amount ranging from about 0.1 to 2.0 moles per liter.

8. The method of claim 6 wherein the liposome forming lipids are present in an amount ranging from about 1.0 to 50 millimoles per liter.

9. The method of claim 6 wherein the liposomal composition is administered in a dosage ranging from about 1.0 to 50 milligrams per kilogram body weight.

10. The method of claim 6 wherein the magnesium salt is selected from the group consisting of magnesium sulfate and magnesium chloride.

11. The method of claim 6 wherein the liposome forming lipids are phospholipids.

12. The method of claim 6 wherein the patient has hypomagnesemia.

13. A method for treating hypomagnesemia comprising the step of enterally administering to a patient suffering from same a liposomal composition comprising a therapeutically effective amount of a magnesium salt, and liposome forming lipids in an amount sufficient to encapsulate the magnesium salt.

14. The method of claim 13 wherein the magnesium salt is selected from the group consisting of magnesium sulfate and magnesium chloride.

15. The method of claim 13 wherein the liposome forming lipids are phospholipids.

* * * * *